(12) United States Patent
Menge

(10) Patent No.: US 10,815,194 B2
(45) Date of Patent: Oct. 27, 2020

US010815194B2

(54) PROCESS FOR THE PREPARATION OF MONO-PROTECTED α,ω-DIAMINO ALKANES

(71) Applicant: Byondis B.V., Nijmegen (NL)

(72) Inventor: Wiro Michael Petrus Bernardus Menge, Nijmegen (NL)

(73) Assignee: Byondis B.V., Nijmegen (NL)

( * ) Notice: Subject to any disclaimer, the term of this patent is extended or adjusted under 35 U.S.C. 154(b) by 42 days.

(21) Appl. No.: 16/348,779

(22) PCT Filed: Nov. 3, 2017

(86) PCT No.: PCT/EP2017/078132
§ 371 (c)(1),
(2) Date: May 9, 2019

(87) PCT Pub. No.: WO2018/086993
PCT Pub. Date: May 17, 2018

(65) Prior Publication Data
US 2020/0010408 A1    Jan. 9, 2020

(30) Foreign Application Priority Data
Nov. 14, 2016    (EP) ..................................... 16198696

(51) Int. Cl.
*C07C 269/06*     (2006.01)
*A61K 47/68*     (2017.01)

(52) U.S. Cl.
CPC ........ *C07C 269/06* (2013.01); *A61K 47/6889* (2017.08)

(58) Field of Classification Search
None
See application file for complete search history.

(56) References Cited

U.S. PATENT DOCUMENTS

2003/0060632 A1*   3/2003   Hu ........................ C07C 237/10
                                                                                                   546/223

FOREIGN PATENT DOCUMENTS

WO   WO2009138985   11/2009
WO   WO2011133039   10/2011
WO   WO2015177360   11/2015

OTHER PUBLICATIONS

K. A. Sacksteder et al., Future Microbiol., 2012, 7(7), 823-837.
B. Malgesini et al., Macromol. Biosci., 2003, 3, 59-66.
D. A. Tomalia et al., Polymer Journal, 1985, 17, 117-132.
F. M. H. de Groot et al., J. Med. Chem., 2000, 43 (16), 3039-3102.
S. C. Jeffrey et al., ACS Med. Chem. Lett., 2010, 1, 277-280.
F. M. H. de Groot et al., J. Org. Chem., 2001, 66(26), 8815-8830.
R. Elgersma et al., Mol. Pharmaceutics, 2015, 12, 1813-1835.
E. R. Burkhardt et al., Chem. Rev., Am. Chem. Soc., 2006, 106(7), 2617-2650.
P. G. M. Wuts and T. W. Greene in Greene's Protective Groups in Organic Synthesis, Fourth Edition, 2006 (ISBN: 978-0-471-69754-1).
Ayman El-Faham et al., Chem. Rev., 2011, 111, 6557-6602.
L. Ducry et al., Bioconjug Chem. 2010, 21(1), 5-13.
Drug Delivery in Oncology: From Basic Research to Cancer Therapy, F. Kratz, et al., p. 558-561.
A.K. Ghosh et al. in J. Med Chem. 2015, 58, 2895-2940.
So-Yeop et al., Tetrahedron, 2004, 60, 2447-2467.

* cited by examiner

*Primary Examiner* — Sudhakar Katakam
*Assistant Examiner* — Jennifer C Sawyer
(74) *Attorney, Agent, or Firm* — Buscher Patent PLLC

(57) ABSTRACT

The present invention relates to a process for the synthesis of mono-protected α,ω-diamino alkanes, the use of said process in a process for the synthesis of a linker drug comprising an α,ω-diamino alkane moiety and the use of the process of the present invention in a process for preparing an antibody-drug conjugate comprising an α,ω-diamino alkane moiety.

20 Claims, No Drawings

PROCESS FOR THE PREPARATION OF MONO-PROTECTED α,ω-DIAMINO ALKANES

FIELD OF THE INVENTION

The present invention relates to an improved process for the preparation of mono-protected α,ω-diamino alkanes.

BACKGROUND OF THE INVENTION

α,ω-Diamino alkanes are important synthetic intermediates used in organic chemistry. They are used in the synthesis of, e.g. the antitubercular drugs ethambutol and SQ109 (K. A. Sacksteder et al., Future Microbiol., 2012, 7(7), 823-837), in polymers, e.g. 2,2-bis(acrylamido)acetic acid (BAC) and 1,4-bis(acryloyl)piperazine (BP) copolymerized with N-triphenylmethyl-monosubstituted 1,2-diamines (B. Malgesini et al., Macromol. Biosci., 2003, 3, 59-66), and dendrimers such as poly(amidoamine) dendrimer (D. A. Tomalia et al., Polymer Journal, 1985, 17, 117-132).

Additionally, α,ω-diamino alkanes are applied as self-eliminating cyclization spacers in prodrugs (F. M. H. de Groot et al., J. Med. Chem., 2000, 43 (16), 3039-3102, S. C. Jeffrey et al., ACS Med. Chem. Lett., 2010, 1, 277-280). Such spacers have the following structure:

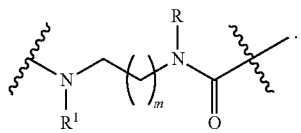

Prodrugs containing a spacer system composed of an α,ω-diamino alkane cyclization spacer and an electronic cascade spacer have shown an enhanced release rate of the active drug after enzymatic activation (F. M. H. de Groot et al., J. Org. Chem., 2001, 66(26), 8815-8830). Fast release of the active drug at the target site is especially important in the field of antibody-drug conjugates (ADCs).

The plasma stability of ADCs comprising an α,ω-diamino alkane as self-eliminating cyclization spacer depends on the substitution on the amines of the α,ω-diamino alkane. ADCs in which the substitution on these amines is asymmetrical show the highest plasma stability (R. Elgersma et al., Mol. Pharmaceutics, 2015, 12, 1813-1835).

For the synthesis of compounds comprising asymmetrically substituted α,ω-diamino alkanes moieties, it is necessary to use an α,ω-diamino alkane wherein one amino group is protected, i.e. a mono-protected derivative, to prevent formation of two different compounds, which is not the case for the synthesis of compounds comprising symmetrical α,ω-diamino alkyl moieties. However, it is still advantageous to use a mono-protected α,ω-diamino alkane for the synthesis of compounds comprising symmetrical α,ω-diamino alkyl moieties, because in a process step entailing coupling unprotected symmetrical α,ω-diamino alkanes to a molecule, the use of an excess of the unprotected symmetrical α,ω-diamino alkane is necessary to prevent formation of side products. When using a mono-protected α,ω-diamino alkane there is no need for such excess.

The currently known processes for the synthesis of mono-protected α,ω-diamino alkanes, however, present several disadvantages.

WO2011133039 in Example 1 describes the synthesis of mono-protected α,ω-diamino alkanes via either reductive amination (Route A) or via alkylation (Route B).

The yields of mono-protected α,ω-diamino alkanes through Route A are low (27-63%) due to difficulties in purification. Moreover, the Swern reaction is performed at a temperature of −60° C., which is not preferred on an industrial scale, e.g. the reaction involves the use of DMSO, a solvent that is not easily removed; and the reaction involves aldehyde intermediates which are instable and therefore problematic to handle and purify. As a result, the reductive amination process requires two unavoidable and difficult chromatographic purification steps.

Route B also provides mono-protected α,ω-diamino alkanes in low yields and presents several additional disadvantages. Particularly, decomposition of the intermediate mesylate and over-alkylation (two-fold alkylation of the amine) are observed, leading to various side-products. Difficult chromatographic purification for the separation of the desired product from the side-products is therefore unavoidable. Moreover, the last step of the process is performed overnight at a temperature of 60° C.; such conditions are not preferred on an industrial scale.

Hence, there is a need for an improved process for preparing mono-protected α,ω-diamino alkanes. In particular, it would be desirable to have a process which is efficient in terms of yield and chemical purity, cost effective in terms of reagents and reaction conditions, and which is applicable on an industrial scale.

BRIEF DESCRIPTION OF THE INVENTION

The present invention relates to a process for the synthesis of mono-protected α,ω-diamino alkanes, the use of said process in a process for the synthesis of a linker drug comprising an α,ω-diamino alkane moiety and the use of the process of the present invention in a process for preparing an antibody-drug conjugate comprising an α,ω-diamino alkane moiety.

DETAILED DESCRIPTION OF THE INVENTION

α,ω-Diamino alkanes, and especially mono-protected α,ω-diamino alkanes, are important synthetic intermediates used in organic chemistry. Inter alia, α,ω-diamino alkanes are applied as self-eliminating cyclization spacers in prodrugs, such as ADCs.

ADCs containing a spacer system composed of an α,ω-diamino alkane as cyclization spacer and an electronic cascade spacer have shown an enhanced release rate of the active drug after enzymatic activation.

For the synthesis of such α,ω-diamino alkane containing prodrugs, it is advantageous to use an α,ω-diamino alkane wherein one amino group is protected, i.e. a mono-protected α,ω-diamino alkane.

In one embodiment, the invention relates to a process for the synthesis of a compound of formula (III)

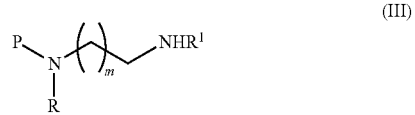

(III)

comprising the steps of: a) converting a compound of formula (I) into a compound of formula (II) by reacting a compound of formula (I) with a compound of formula (IV) in the presence of a coupling reagent

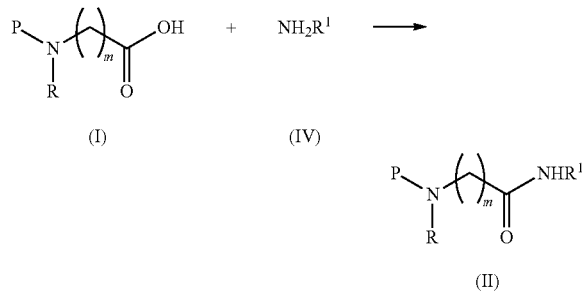

b) treating, the compound of formula (II) with a borane reagent, followed by acid hydrolysis; wherein R and $R^1$ are independently selected from H, $(CH_2)_nOCH_3$, $(CH_2CH_2O)_nH$, $(CH_2CH_2O)_nCH_3$, $(CH_2)_nNHP$, $(CH_2)_nN(CH_3)_2$, $(CH_2)_nNHCONH_2$, $(CH_2)_nNHSO_2CH_3$, $(CH_2)_nSO_2NH_2$, optionally substituted $C_{1-8}$ alkyl, optionally substituted $C_{3-15}$ cycloalkyl and optionally substituted $C_{3-15}$ heterocycloalkyl; P is a protective group;
m is an integer of from 1 to 3; and
n is an integer of from 1 to 12.

The starting materials of the present invention, i.e. a compound of formula (I) and (IV) are either commercially available or can be produced by methods and procedures well-known in the prior art.

In the generic structures throughout this description and in the claims, letters other than R, $R^1$, and $R^2$ are used to define structural elements. To prevent these letters to be mistaken as representing an atom, they are given in bold typeface when they do not represent an atom.

The design of the synthesis route allows the combination of a high yielding peptide coupling step and an efficient boron reduction step (see E. R. Burkhardt et al., Chem. Rev., Am. Chem. Soc., 2006, 106(7), 2617-2650 for such boron reduction step). With the process of the present invention, the compounds of formula (III) can be prepared in a yield higher than 70%, preferably higher than 75%, more preferably higher than 80%; and with a chemical purity higher than 90% without requiring any chromatographic purification steps.

The term "alkyl" as used throughout the present specification refers to a linear or branched saturated hydrocarbon chain. Suitable examples of $C_{1-8}$ alkyl groups include methyl, ethyl, isopropyl and butyl.

The term "cycloalkyl" as used throughout the present specification refers to a cyclic saturated hydrocarbon chain. Suitable examples of cycloalkyl groups include cyclopropane, cyclobutane, cyclopentane, cyclohexane, cycloheptane and cyclooctane.

The term "heterocycloalkyl" as used throughout the present specification refers to a cyclic saturated hydrocarbon chain in which one or more carbons are replaced by a heteroatom. Suitable examples of heteroatoms include N, O and S.

The term "cyclic saturated hydrocarbon" as used throughout the present specification refers to cyclic compounds wherein all the atoms that make up the cyclic compound are single bonded to the other atoms, with no double or triple bonds.

The term "substituted", when used as an adjective to "alkyl", "cycloalkyl", or "heterocycloalkyl", indicates that said "alkyl", "cycloalkyl", or "heterocycloalkyl" contains one or more substituents that substitute hydrogen. Exemplary substituents include OH, $C_{1-8}$ alkyl and $(CH_2CH_2O)_iH$, wherein i is an integer of from 1 to 6.

In a preferred embodiment of the present invention, R and $R^1$ are independently selected from H, $(CH_2)_nOCH_3$, $(CH_2CH_2O)_nH$, $(CH_2CH_2O)_nCH_3$, $(CH_2)_nNHP$, $(CH_2)_nN(CH_3)_2$, $(CH_2)_nNHCONH_2$, $(CH_2)_nNHSO_2CH_3$, $(CH_2)_nSO_2NH_2$, optionally substituted $C_{1-8}$ alkyl, optionally substituted $C_{3-15}$ cycloalkyl and optionally substituted $C_{3-15}$ heterocycloalkyl, and wherein n is an integer of from 1 to 12, preferably n is an integer of from 1 to 6.

In a second preferred embodiment of the present invention, R and $R^1$ are independently selected from H, $(CH_2)_nOCH_3$, $(CH_2CH_2O)_nH$, $(CH_2CH_2O)_nCH_3$, and optionally substituted $C_{1-8}$ alkyl, and wherein n is an integer of from 1 to 12, preferably n is an integer of from 1 to 6.

In a third preferred embodiment of the present invention, R is $C_{1-8}$ alkyl and $R^1$ is selected from H, $(CH_2)_nOCH_3$, $(CH_2CH_2O)_nH$, $(CH_2CH_2O)_nCH_3$, $(CH_2)_nNHP$, $(CH_2)_nN(CH_3)_2$, $(CH_2)_nNHCONH_2$, $(CH_2)_nNHSO_2CH_3$, $(CH_2)_nSO_2NH_2$, optionally substituted $C_{1-8}$ alkyl, optionally substituted $C_{3-15}$ cycloalkyl, and optionally substituted $C_{3-15}$ heterocycloalkyl; wherein n is an integer of from 1 to 12, preferably n is an integer of from 1 to 6.

In a further preferred embodiment of the present invention, R is $CH_3$ and $R^1$ is selected from $(CH_2)_nOCH_3$, $(CH_2CH_2O)_nH$, $(CH_2CH_2O)_nCH_3$, and optionally substituted $C_{1-8}$ alkyl; wherein n is an integer of from 1 to 12, preferably n is an integer of from 1 to 6.

In a further preferred embodiment of the present invention, R is $CH_3$ and $R^1$ is selected from $(CH_2CH_2O)_nH$, $(CH_2CH_2O)_nCH_3$, and optionally substituted $C_{1-8}$ alkyl; wherein n is an integer of from 1 to 12, preferably n is an integer of from 1 to 6.

Typically, P is an amine-protective group. Suitable amine-protective groups are extensively described in literature, e.g. by P. G. M. Wuts and T. W. Greene in Greene's Protective Groups in Organic Synthesis, Fourth Edition, 2006 (ISBN: 978-0-471-69754-1).

The person skilled in the art will be able to select suitable protective groups to be used in accordance with the process of the present invention.

In an embodiment of the present invention, P is selected from the group consisting of 1,1-dimethyl-2-haloethyl carbamate, 1,1-dimethyl-2,2-dibromoethyl carbamate, t-butyl carbamate, 1-adamantyl carbamate, N-(2-pivaloylamino)-1,1-dimethylethyl carbamate, 2-[(2-nitrophenyl)dithio]-1-phenylethyl carbamate, 9-anthrylmethyl carbamate, methyl carbamate, ethyl carbamate, p-methoxybenzyl carbamate, N-hydroxypiperidinyl, p-nitrobenzyl carbamate, diphenylmethyl carbamate, m-chloro-p-acyloxybenzyl carbamate, p-(dihydroxyboryl) benzyl carbamate, 5-benzisoxazolylmethyl carbamate, benzyl, N-2,4,6-trimethylbenzenesulfonyl, N-toluenesulfonyl, N-benzylsulfonyl and N-trifluoromethylsulfonyl.

Preferably, P is selected from the group consisting of 1,1-dimethyl-2-haloethyl carbamate, 1,1-dimethyl-2,2-dibromoethyl carbamate, t-butyl carbamate, 1-adamantyl carbamate, N-(2-pivaloylamino)-1,1-dimethylethyl carbamate, 2-[(2-nitrophenyl)dithio]-1-phenylethyl carbamate and 9-anthrylmethyl carbamate.

More preferably, P is t-butyl carbamate (Boc).

In one embodiment, the process in accordance with the invention is used for the synthesis of a compound of formula (III) selected from

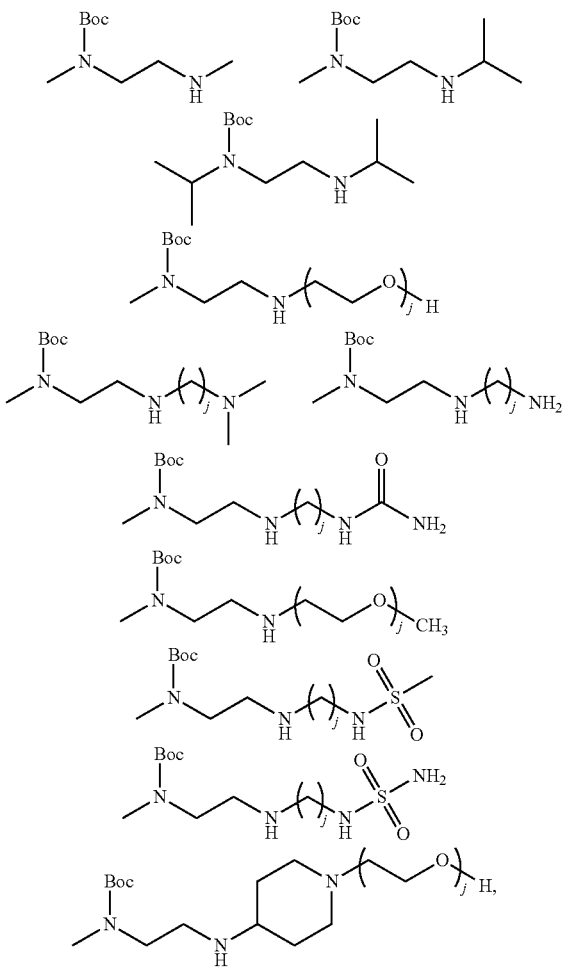

wherein j is an integer of from 1 to 12, preferably of from 1 to 6.

In a preferred embodiment, the process in accordance with the invention is used for the synthesis of a compound of formula (III) selected from

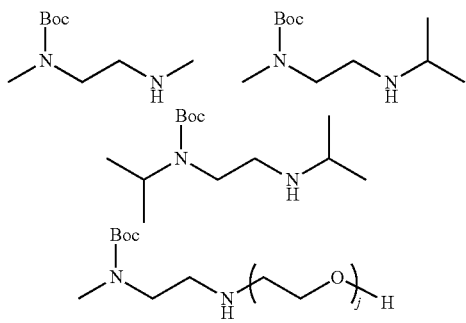

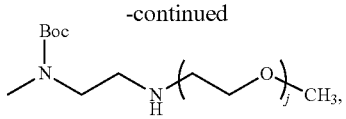

wherein j is an integer of from 1 to 12, preferably of from 1 to 6.

More preferably, the process in accordance with the invention is used for the synthesis of a compound of formula (III) selected from

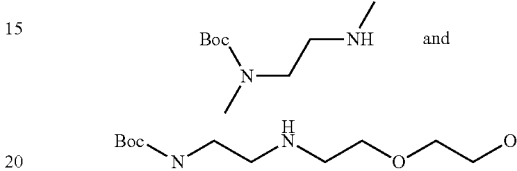

Even more preferably, the process in accordance with the invention is used for the synthesis of a compound of formula (III), which is

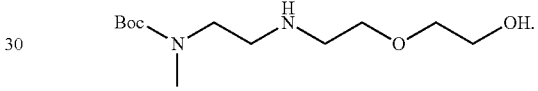

The term "coupling reagent" as used throughout the present specification means a peptide coupling reagent known to the person skilled in the art. Suitable peptide coupling reagents are carbodiimide reagents, phosphonium reagents and aminium reagents. Suitable examples are described in literature, e.g. in Ayman El-Faham et al., Chem. Rev., 2011, 111, 6557-6602.

A preferred coupling reagent is a carbodiimide reagent. More preferred is a carbodiimide reagent selected from the group consisting of DCC (N,N'-dicyclohexyl-carbodiimide), DIC (N,N'-diisopropylcarbodiimide) and EDC (1-[(3-dimethylaminopropyl)]-3-ethylcarbodiimide hydrochloride). The most preferred carbodiimide reagent is EDC.

A suitable phosphonium reagent is selected from the group consisting of BOP (benzotriazol-1-yloxy-tris-(dimethyl-amino)-phosphonium hexafluorophosphate), PyBOP (benzotriazol-1-yloxy-tripyrrolidino-phosphonium hexafluorophosphate), PyBrOP (bromo-tripyrrolidino-phosphonium hexafluorophosphate), PyAOP (7-aza-benzotriazol-1-yloxy-tripyrrolidinophosphonium hexafluorophosphate) and PyOxim (ethyl cyano(hydroxyimino) acetato-O2)-tri-(1-pyrrolidinyl)-phosphonium hexafluorophosphate).

A suitable aminium reagent is selected from the group consisting of TBTU (O-(benzotriazol-1-yl)-1,1,3,3-tetramethyluronium tetrafluoroborate), HCTU (2-(6-chloro-1H-benzotriazol-1-yl)-N,N,N',N'-tetramethyluronium hexafluorophosphate), HDMC (N-[(5-chloro-1H-benzotriazol-1-yl)-dimethylamino-morpholino]-uronium hexafluorophosphate N-oxide), HATU (O-(7-azabenzotriazol-1-yl)-1,1,3,3-tetramethyl-uronium hexafluorophosphate), COMU (1-[1-(cyano-2-ethoxy-2-oxoethylideneaminooxy)-dimethylamino-morpholino]-uronium hexafluorophosphate), TOTT (2-(1-oxy-pyridin-2-yl)-1,1,3,3-tetramethylisothiouronium tetrafluoroborate), HBTU (N,N,N',N'-tetramethyl-O-(1H-benzotriazol-1-yl)uronium hexafluorophosphate) and TFFH (fluoro-N,N,N',N'-tetramethylformamidinium hexafluorophosphate). In the present invention, the aminium reagent for use in the coupling reaction may be used with or without a base.

A suitable solvent for use in the coupling reaction is without limitation an organic solvent, preferably a polar aprotic solvent. Preferably, the solvent is selected from the group consisting of DMA (N,N-dimethylacetamide), DMF (dimethylformamide), DMSO (dimethyl sulfoxide), NMP (methylpyrrolidone), HMPA (hexamethylphosphoramide), methyl ethyl ketone, acetonitrile, THF (tetrahydrofuran), DCM (dichloromethane), acetone, EtOAc (ethyl acetate) and 2-butanone. A preferred solvent is DCM.

A typical reaction temperature of from 0 to 40° C. can be used. In a specific embodiment of the present invention, the reaction mixture is first cooled to 0° C., the compound of formula (IV) is added, and then the reaction mixture is allowed to warm to room temperature.

The term "room temperature" as used throughout the present specification is a temperature between 17° C. and 27° C.

A suitable borane reagent for the reaction with the compound of formula (II) is borane, diborane or a borane-ligand complex. Preferably, the borane-ligand complex is borane tetrahydrofuran, 9-borabicyclo[3.3.1]nonane (9-BBN) or a borane sulfide. More preferred borane-ligand complexes are borane tetrahydrofuran or borane dimethyl sulfide. Borane dimethyl sulfide is a particularly preferred borane-ligand complex. In accordance with the present invention, the borane, diborane or a borane-ligand complex is used in an amount of from 1 to 10 equivalents. The person skilled in the art will be able to select a suitable amount of borane, diborane or a borane-ligand complex to be used in accordance with the process of the present invention.

In a preferred embodiment of the present invention, the reaction is carried out using about 5 equivalents of borane dimethyl sulfide.

A suitable solvent for the reaction of a compound of formula (II) with the borane reagent is without limitation an organic solvent, preferably an aprotic solvent. A preferred solvent is an ethereal solvent, particularly preferred is THF.

Typically, a reaction temperature of from 0 to 50° C. can be used. In a specific embodiment of the present invention, the reaction mixture is first cooled to 0° C., the boron reagent is added, and then the mixture is allowed to warm to room temperature. The mixture is subsequently stirred at room temperature.

The obtained borane-intermediate is hydrolyzed by acid hydrolysis providing the cyclization spacer compound of formula (III). In accordance with the present invention, a suitable acid to be used for said acid hydrolysis is a strong mineral or organic acid.

Advantageously, the suitable acid is selected from the group consisting of alkyl or optionally substituted alkyl sulfonic acid, aryl or optionally substituted aryl sulfonic acid, potassium hydrogen sulphate, sulphuric acid, hydrochloric acid, hydrobromic acid, phosphoric acid, trifluoroacetic acid, trichloroacetic acid, chloroacetic acid, phosphonic acid, benzyl phosphoric acid, acetic acid, and formic acid.

A preferred acid is selected from the group consisting of alkyl or optionally substituted alkyl sulfonic acid and aryl or optionally substituted aryl sulfonic acid.

In a more preferred embodiment of the present invention, the acid is an alkyl or optionally substituted alkyl sulfonic acid selected from the group consisting of methanesulfonic acid, ethanesulfonic acid, camphor sulfonic acid, nonafluorobutane-1-sulfonic acid and 2-hydroxyethanesulfonic acid.

In an even more preferred embodiment of the present invention, the acid is an aryl or optionally substituted aryl sulfonic acid selected from the group consisting of benzenesulfonic acid, 4-toluenesulfonic acid and naphthalenesulfonic acid.

In a most preferred embodiment, the acid is 4-toluenesulfonic acid.

The acidic hydrolysis may proceed in an organic solvent, water or a mixture of both. A preferred solvent is a lower alcohol (i.e. a $C_1$-$C_4$ aliphatic alcohol) and a particularly preferred solvent is MeOH (methanol). A reaction temperature of from 0 to 80° C. can be used, but in a preferred embodiment of the present invention, the reaction is carried out at a temperature below 30° C. In a further preferred embodiment of the present invention, the reaction is carried out at a temperature between 17° C. and 27° C. In a specific embodiment of the present invention, the reaction is carried out at 25° C.

A skilled person in the art will be able to select a suitable acid and a suitable solvent to carry the hydrolysis at a temperature below 30° C.

In an additional embodiment, the process for the synthesis of a compound of formula (III) is used in a process for the synthesis of a linker drug of formula (VIII)

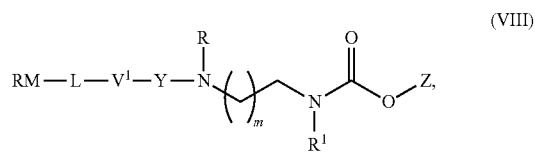

(VIII)

wherein RM is a reactive moiety;

L is a linking group linking RM to $V^1$;

$V^1$ is a peptide, a mono, di-, or oligosaccharide;

Y is either absent or an electronic cascade spacer;

Z is a therapeutic or diagnostic moiety;

R and $R^1$ are independently selected from H, $(CH_2)_nOCH_3$, $(CH_2CH_2O)_nH$, $(CH_2CH_2O)_nCH_3$, $(CH_2)_nNHP$, $(CH_2)_nN(CH_3)_2$, $(CH_2)_nNHCONH_2$, $(CH_2)_nNHSO_2CH_3$, $(CH_2)_nSO_2NH_2$, optionally substituted $C_{1-8}$ alkyl, optionally substituted $C_{3-15}$ cycloalkyl and optionally substituted $C_{3-15}$ heterocycloalkyl;

P is a protective group;

m is an integer of from 1 to 3; and n is an integer of from 1 to 12.

Preferably, n is an integer of from 1 to 6.

In the present invention, RM is a reactive moiety. The term "reactive moiety" herein refers to a functional group that can react with a second functional group under relatively mild conditions and without the need of prior functionalization of the reactive moiety. Examples of reactive moieties include, but are not limited to, carbamoyl halide, acyl halide, active ester, anhydride, α-haloacetyl, α-haloacetamide, maleimide, isocyanate, isothiocyanate, disulfide, thiol, hydrazine, hydrazide, sulfonyl chloride, aldehyde, methyl ketone, vinyl sulfone, halomethyl, and methyl sulfonate.

Preferably, RM is selected from the group consisting of

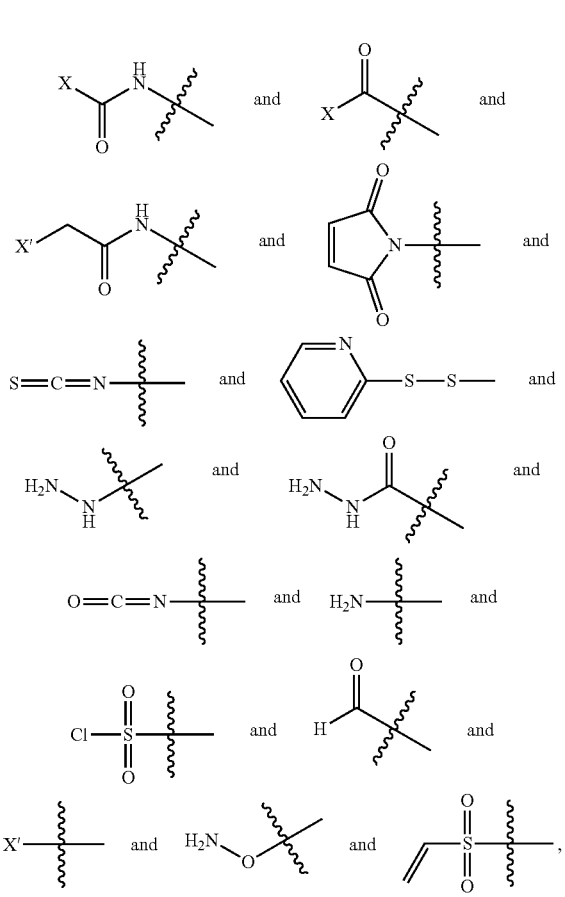

wherein

X is selected from halide, hydroxyl, OC(O)R$^a$, and OC(O)OR$^a$, or C(O)—X is an active ester;

X' is selected from halide, mesyloxy, triflyloxy and tosyloxy; and

R$^a$ is selected from optionally substituted C$_{1-10}$ alkyl, C$_{1-10}$ heteroalkyl, C$_{3-10}$ cycloalkyl, C$_{1-10}$ heterocycloalkyl, C$_{5-10}$ aryl, and C$_{1-10}$ heteroaryl.

In a more preferred embodiment, RM is selected from

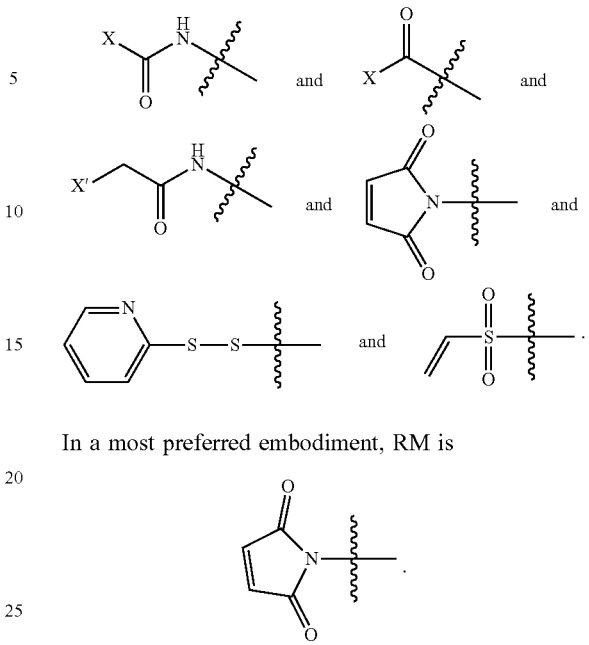

In a most preferred embodiment, RM is

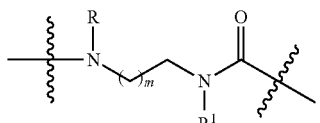

In the present invention, L is a linking group. The term "linking group" refers to a chemical structure which covalently binds the building block RM to V$^1$. Together with V$^1$, Y and the diamine below L constitutes the spacer system (linker) which covalently binds the building block RM to Z. Such a spacer system may be used in antibody drug conjugates (ADCs) (L. Ducry et al., Antibody-drug conjugates: linking cytotoxic payloads to monoclonal antibodies. Bioconjug Chem. 2010, 21(1), 5-13).

Preferably, L is selected from the group consisting of

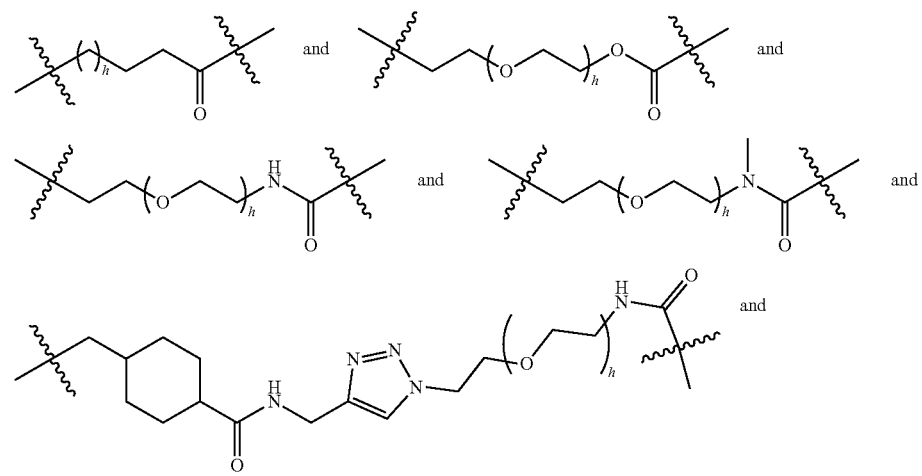

-continued

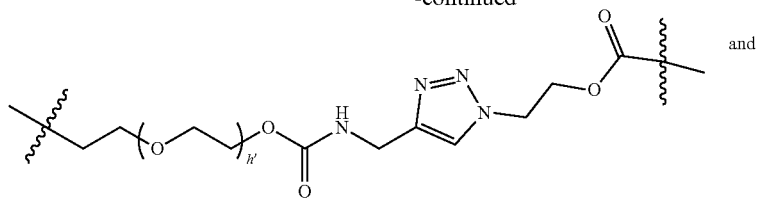
and

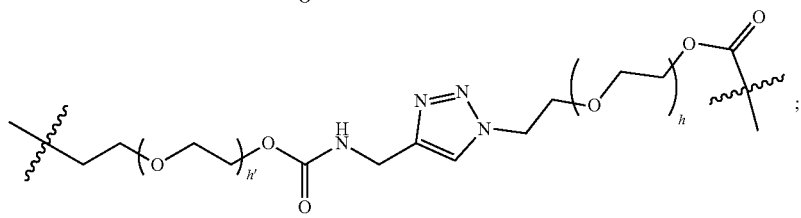
;

wherein h and h' each independently range of from 1 to 8.

More preferably, L is selected from the group consisting of

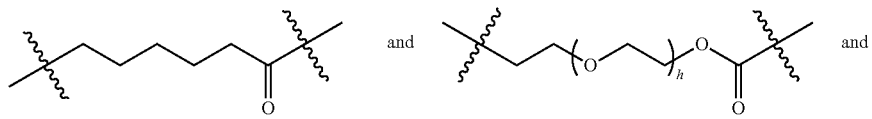
and and and

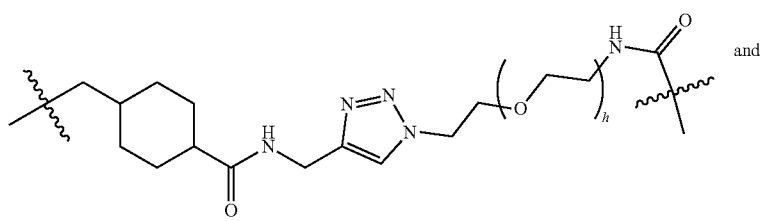

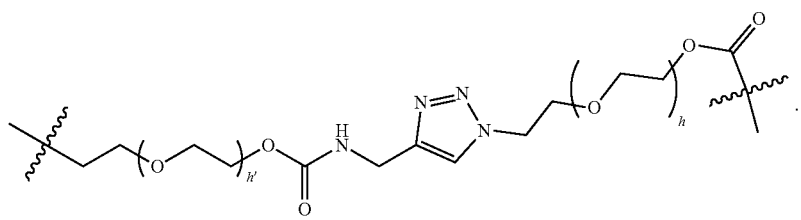

In a most preferred embodiment, L is

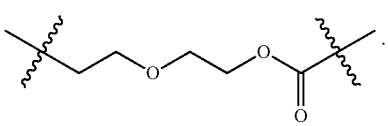 [SMILES: *CCOCCOC(*)=O]

$V^1$ is a peptide, or a mono, di-, or oligosaccharide.

In a preferred embodiment of the invention, $V^1$ is a peptide. In a more preferred embodiment, $V^1$ is a dipeptide selected from valylcitrulline, valyllysine, phenylalanylysine, alanylphenylalanylysine, and D-alanylphenylalanylysine. In a most preferred embodiment, the moiety $V^1$ is valylcitrulline.

Y is either absent or an electronic cascade spacer. The term "electronic cascade spacer" refers to a self-elimination spacer, either branched or unbranched, which may self-eliminate through one or more 1,2+2n electronic cascade eliminations (n≥1) e.g., Suitable electronic cascade spacers are known in the art and may be found in e.g. F. M. H. de Groot et al., Elongated Multiple Electronic Cascade and Cyclization Spacer Systems in Activatible Anticancer Prodrugs for Enhanced Drug Release, J. Org. Chem. 2001, 66, 8815-8830 and Drug Delivery in Oncology: From Basic Research to Cancer Therapy, F. Kratz, et al., p. 558-561. Typically, the electronic cascade spacer comprises a phenyl ring or a heterocyclic aromatic ring substituted with a strong electron donating group and is linked on the ortho or para position to a leaving group via a $CH_2$ or a conjugated system to a leaving group, e.g p-aminobenzyloxy carbonyl.

In a preferred embodiment, Y is selected from the group consisting of

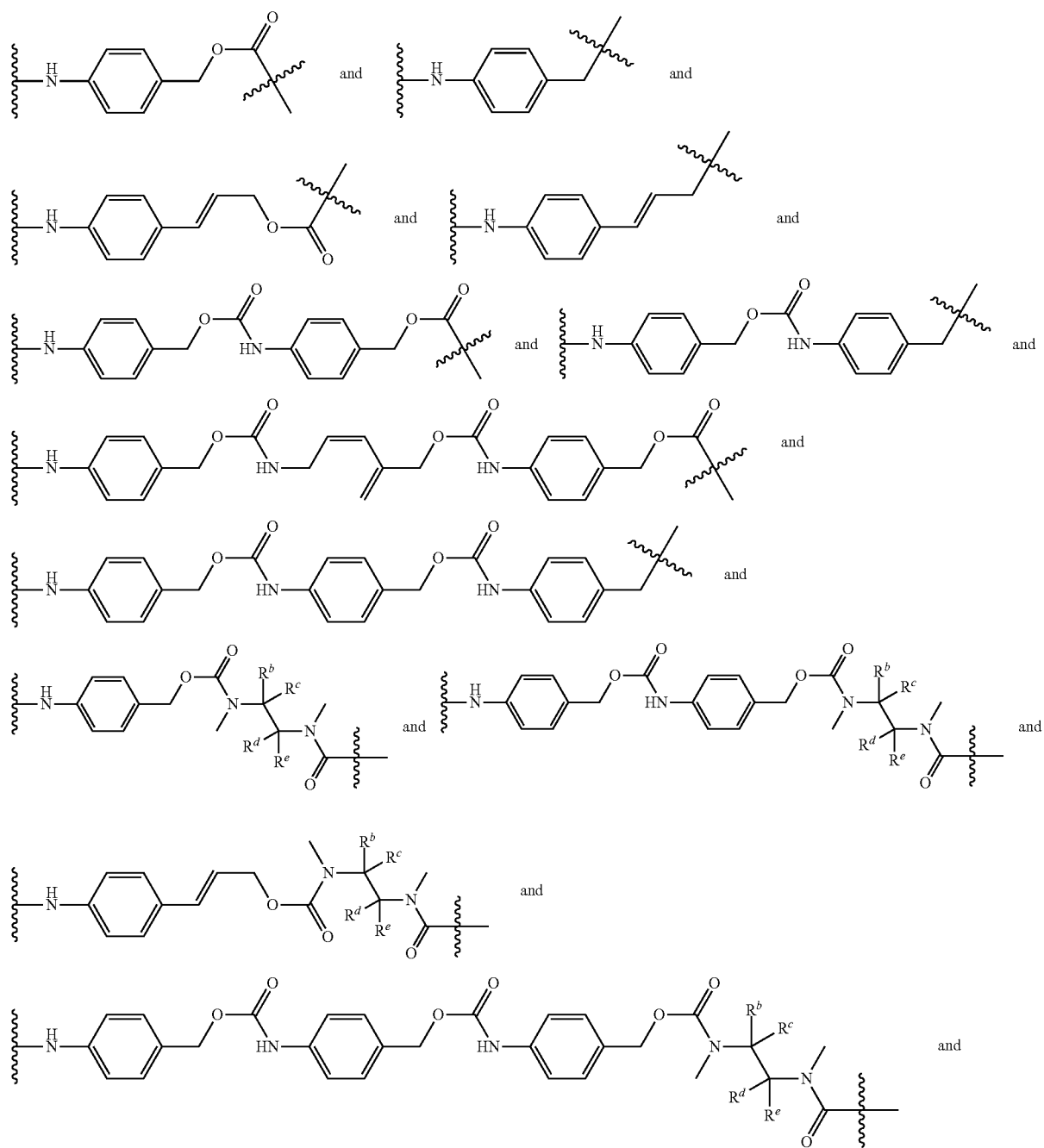
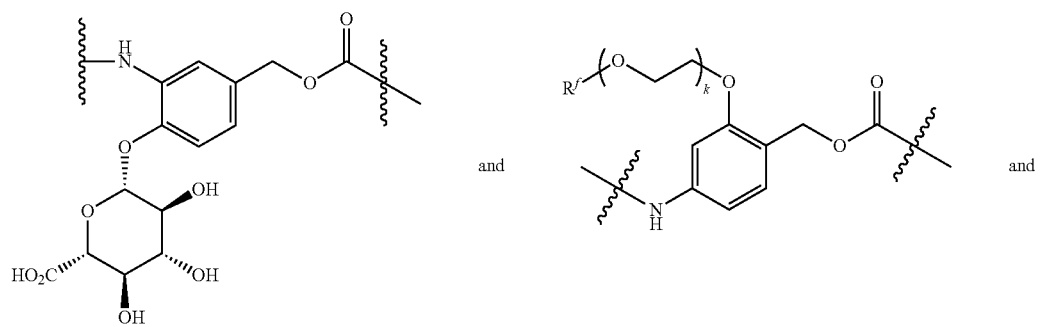

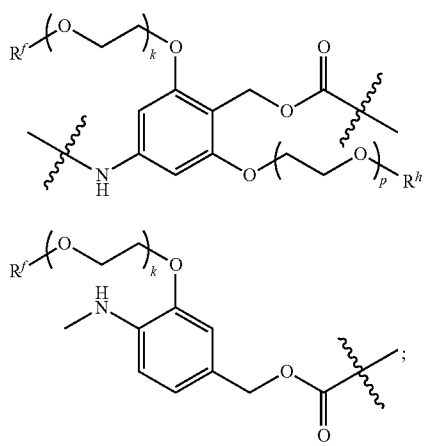
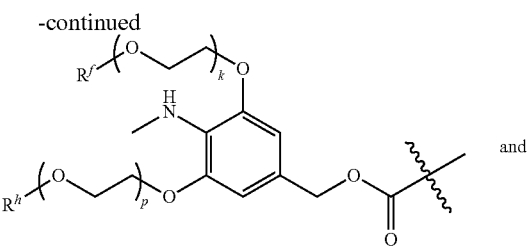

and

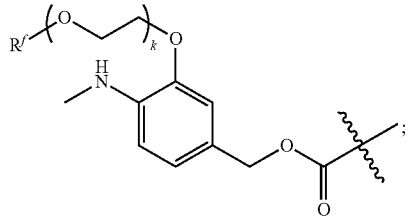

;

wherein $R^b$, $R^c$, $R^d$, and $R^e$ are independently selected from H, OH, SH, $NH_2$, $N_3$, $NO_2$, NO, $CF_3$, CN, $C(O)NH_2$, $C(O)H$, $C(O)OH$, halogen, $R^z$, $SR^z$, $S(O)R^z$, $S(O)_2R^z$, $S(O)OR^z$, $S(O)_2OR^z$, $OS(O)R^z$, $OS(O)_2R^z$, $OS(O)OR^z$, $OS(O)_2OR^z$, $OR^z$, $NHR^z$, $N(R^z)R^{z1}$, $^+N(R^z)(R^{z1})R^{z2}$, $P(O)(OR^z)(OR^{z1})$, $OP(O)(OR^z)(OR^{z1})$, $C(O)R^z$, $C(O)OR^z$, $C(O)N(R^{z1})R^z$, $OC(O)R^z$, $OC(O)OR^z$, $OC(O)N(R^z)R^{z1}$, $N(R^{z1})C(O)R^z$, $N(R^{z1})C(O)OR^z$, and $N(R^{z1})C(O)N(R^{z2})R^z$; wherein $R^z$, $R^{z1}$, and $R^{z2}$ are independently selected from H and optionally substituted $C_{1-6}$ alkyl, $C_{1-6}$ heteroalkyl, $C_{3-20}$ cycloalkyl, $C_{1-20}$ heterocycloalkyl, $C_{6-20}$ aryl, or $C_{1-20}$ heteroaryl, $R^z$, $R^{z1}$, and $R^{z2}$ optionally being joined by one or more bonds to form one or more optionally substituted carbocycles and/or heterocycles, two or more of the substituents $R^b$, $R^c$, $R^d$, and $R^e$ optionally being joined by one or more bonds to form one or more optionally substituted carbocycles and/or heterocycles;
$R^f$ and $R^h$ are independently selected from H and methyl; and
k and p are independently an integer of from 0 to 10.

In a more preferred embodiment, Y is selected from the group consisting of:

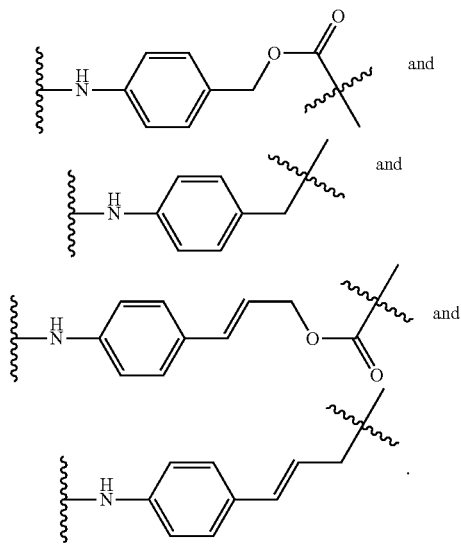

In a most preferred embodiment, Y is

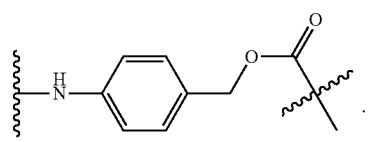 [SMILES: *Nc1ccc(COC(*)=O)cc1]

In the present invention, Z is a therapeutic or diagnostic moiety.

The term "diagnostic moiety" refers to a substance used for the analysis or detection of a disease or other medical condition.

The term "therapeutic moiety" refers to a substance used for the treatment of a disease or condition. Preferably, the therapeutic moiety Z is an anti-proliferative or anti-cancer agent such as a cytotoxic agent, cytostatic agent, anti-angiogenic agent, and radiotherapeutic agent.

In a preferred embodiment, Z is a maytansinoid, an auristatin, a dolastatin, a trichothecene, a duocarmycin derivative, a duocarmycin dimer, a pyrrolobenzodiazepine, α-amanitin, a doxorubicin, a calicheamicin or other enediyne antibiotic, a taxane, an anthracycline, or a stereoisomer, isostere, analog or derivative thereof.

In one embodiment, Z is a duocarmycin derivative.
In a preferred embodiment of the invention, Z is

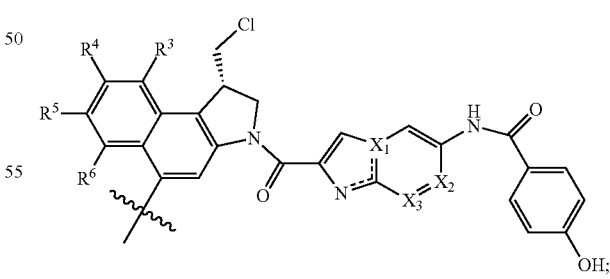

wherein $R^3$ is $CH_3$, $CH_2CH_3$, $OCH_3$, $OCH_2CH_3$, $CF_3$, $OCF_3$, Cl or F;
$R^4$, $R^5$, $R^6$ are independently H or $C_{1-6}$ alkyl or
$R^3$ and $R^4$ taken together form a 5- or 6-membered (hetero) cycloalkyl group;
$X_1$ is C or N; and
$X_2$ and $X_3$ are independently C or N.

In a most preferred embodiment of the invention, Z is

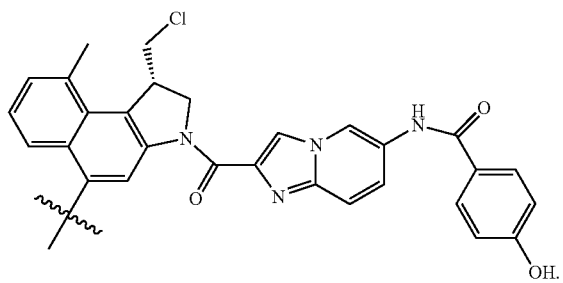 [SMILES: *c1cc2c(c3c(C)cccc13)[C@H](CCl)CN2C(=O)c1cn2cc(NC(=O)c3ccc(O)cc3)ccc2n1]

The process for the synthesis of a linker drug of formula (VIII) as described hereinabove further comprises the step of reacting a compound of formula (IX) with a compound of formula (III) to provide a compound of formula (X)

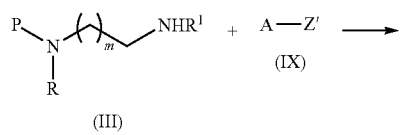

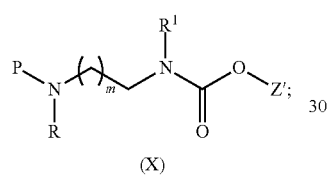

wherein A is an activated carbonate moiety;

Z' is Z or Z' is Z comprising one or more alcohol-protective groups P' when Z comprises multiple hydroxyl functional groups; and R, $R^1$, P and m are as defined hereinabove.

In the present invention, A is an activated carbonate moiety. The term "activated carbonate moiety" refers to a carbonate ester with increased rate of reactivity in a reaction with a nucleophile and comprises a carbonate moiety and a leaving group.

A suitable activated carbonate moiety A to be used in accordance with the invention is known to the person skilled in the art. Examples of suitable activated carbonate moieties can be found in e.g. A. K. Ghosh et al. in J. Med Chem. 2015, 58, 2895-2940.

Preferably, A is selected from the group consisting of

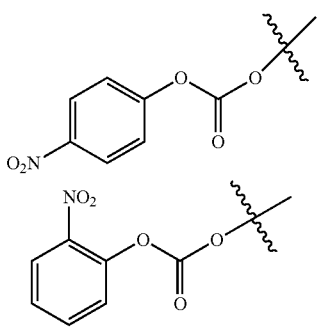

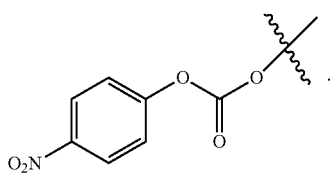 [SMILES: *OC(=O)Oc1ccc([N+](=O)[O-])cc1]

Most preferably, A is

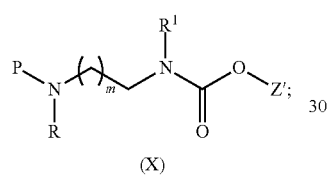

Z' is conveniently prepared by reacting Z with an alkoxycarbonylating agent, e.g. 4-nitrophenyl chloroformate, 2-nitrophenyl chloroformate, pentafluorophenyl chloroformate or bis-(4-nitrophenyl) carbonate, in the presence of base.

In a preferred embodiment of the present invention, Z' is prepared by reacting Z with 4-nitrophenyl chloroformate.

In a preferred embodiment of the present invention, Z' is

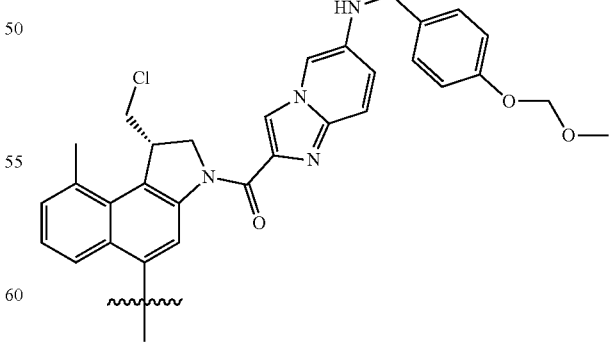

The term "alcohol-protective group" refers to a protective group suitable to protect an alcohol function. Suitable alcohol-protective groups are well-described in literature, e.g. by P. G. M. Wuts and T. W. Greene in Greene's Protective Groups in Organic Synthesis, Fourth Edition, 2006 (ISBN: 978-0-471-69754-1). The person skilled in the art will be able to select suitable protective groups to be used in accordance with the process of the present invention.

A suitable alcohol-protective group to be used in accordance with the process of the present invention is a group which is stable in the presence of a mild base, such as triethylamine, diisopropylethylamine, N-methylmorpholine, pyridine or collidine.

Typically, the alcohol-protective group P' is selected from the group of ethers, esters and carbonates.

In a preferred embodiment of the present invention, P' is an ether selected from the group consisting of MOM (methoxymethyl ether), MTM (methylthiomethyl ether), SMOM [(phenyldimethylsilyl) methoxymethyl ether], BOM (benzyloxymethyl ether), PMBM (p-methoxyenzyloxymethyl ether), p-nitrobenzyloxymethyl ether, NBOM (o-methoxyenzyloxymethyl ether), (4-methoxyphenoxy)methyl ether, GUM (guaiacolmethyl ether), t-butoxymethyl ether, MEM (2-methoxyethoxymethyl ether), 2,2,2-trichloroethoxymethyl ether, bis(2-chloroethoxy)methyl ether, SEM [2-(trimethylsilyl)ethoxymethyl ether], MM (menthoxymethyl ether), THP (tetrahydropyranyl ether), tetrahydrothiopyranyl ether, tetrahydrofuranyl ether, tetrahydrothiofuranyl ether, EE (1-ethoxyethyl ether), CEE [1-(2-chloroethoxy)ethyl ether], SEE {1-[2-(trimethylsilyl)ethoxy]ethyl ether}, MIP (1-methyl-1-methoxyethyl ether), MBE (1-methyl-1-benzyloxyethyl ether), 1-methyl-1-phenoxyethyl ether, 2,2,2-trichloroethyl ether, 2-trimethylsilylethyl ether, 2-(benzylthio)ethyl ether, 2-(phenylselenyl)ethyl ether, t-butyl ether, p-chlorophenyl ether, p-methoxyphenyl ether, p-nitrophenyl ether, benzyl ether, MPM (p-methoxybenzyl ether), DMPM (3,4-dimethoxybenzyl ether), o-nitrobenzyl ether, p-nitrobenzyl ether, 2,6-dichlorobenzyl ether, p-phenylbenzyl ether, 2,6-difluorobenzyl ether, 2-trifluoromethylbenzyl ether, diphenylmethyl ether, triphenylmethyl ether, TMS (trimethylsilyl ether), TES (triethylsilyl ether), TIPS (triisopropylsilyl ether), IPDMS (dimethylisopropylsilyl ether), DEIPS (diethylisopropylsilyl ether), TDS (dimethylthexylsilyl ether), TBDMS (t-butyldimethylsilyl ether), TBDPS (t-butyldiphenylsilyl ether), tribenzylsilyl ether, TPS (triphenylsilyl ether), and DPMS (diphenylmethylsilyl ether); or P' is an ester selected from the group consisting of formate ester, acetate ester, nicotinate ester, 3-phenylpropionate ester, 4-oxopentanoate ester, 4,4-(ethylenedithio)pentanoate ester, pivaloate ester, 1-adamantoate ester, and benzoate ester; or P' is a carbonate selected from the group consisting of methyl carbonate, methoxymethyl carbonate, alkyl 2,2,2,-trichloroethyl carbonate, TCBOC (1,1-dimethyl-2,2,2,-trichloroethyl carbonate), TMSEC [2-(trimethylsilyl)ethyl carbonate], isobutyl carbonate, and benzyl carbonate.

In a more preferred embodiment of the present invention, P' is an ether selected from the group consisting of MOM (methoxymethyl ether), BOM (benzyloxymethyl ether), t-butoxymethyl ether, SEM [2-(trimethylsilyl)ethoxymethyl ether], EE (1-ethoxyethyl ether), SEE {1-[2-(trimethylsilyl)ethoxy]ethyl ether}, t-butyl ether, p-chlorophenyl ether, p-methoxyphenyl ether, benzyl ether, TMS (trimethylsilyl ether), TES (triethylsilyl ether), TIPS (triisopropylsilyl ether) and TBDMS (t-butyldimethylsilyl ether).

In a most preferred embodiment, P' is MOM (methoxymethyl ether).

The reaction between a compound of formula (IX) and a compound of formula (III) is performed in a suitable solvent, preferably in the presence of a base. The base will capture the leaving group. Alternatively, the reaction may be performed using an excess of the compound of formula (III).

Preferably, the base is present in an amount equimolar to the amount of compound (IX).

A suitable base is a tertiary amine, e.g. triethylamine, diisopropylethylamine, N-methylmorpholine, pyridine or collidine. A preferred base is triethylamine.

More preferably, the reaction between a compound of formula (IX) and a compound of formula (III) is performed in the presence of an additive that further activates the carbonate of compound (IX). The additive improves the efficiency of the synthesis. Suitable additives are extensively described in literature (e.g. So-Yeop et al., Tetrahedron, 2004, 60, 2447-2467 and WO2009138985). The person skilled in the art will be able to select a suitable additive to be used in accordance with the process of the present invention.

In a preferred embodiment, the additive is selected from the group consisting of HOBt (hydroxybenzotriazole), HOAt (1-hydroxy-7-azabenzotriazole), HODhbt (3-hydroxy-1,2,3-benzotriazin-4(3H)-one), N-hydroxytetrazole, HOCt (ethyl 1-hydroxy-5-methyl-1H-1,2,3-triazole-4-carboxylate), PTF (triphenyl(phenylmethyl)phosphonium dihydrogentrifluoride) and COMU (ethyl (hydroxyimino)cyanoacetate).

In a more preferred embodiment, the additive is HOBt.

A suitable solvent for the reaction between a compound of formula (IX) and a compound of formula (III) is an aprotic solvent. In a preferred embodiment, the solvent is DCM, trichloromethane, 1,2-dichloroethane, toluene, THF, DME (dimethoxyethane), dioxane, EtOAc, acetonitrile, acetone, DMF or DMA. More preferably, the solvent is THF, dioxane or DMF.

Even more preferably, the solvent is DMF.

In a specific embodiment of the process for the synthesis of a linker drug of formula (VIII), the compound of formula (IX) is

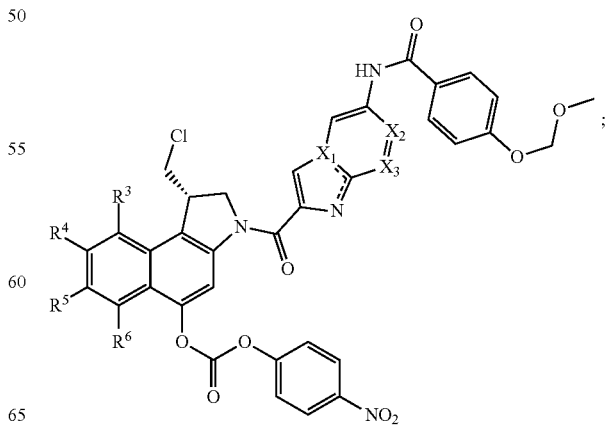

and the compound of formula (X) is

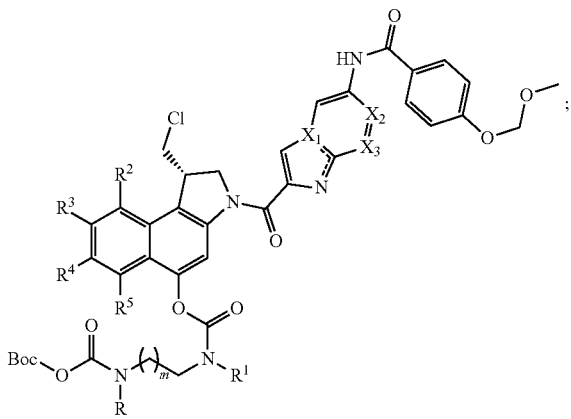

wherein R, $R^1$, $R^2$, $R^3$, $R^4$, $R^5$, $X_1$, $X_2$, $X_3$ and m are as defined hereinabove.

In a further specific embodiment of the invention, the compound of formula (IX) is

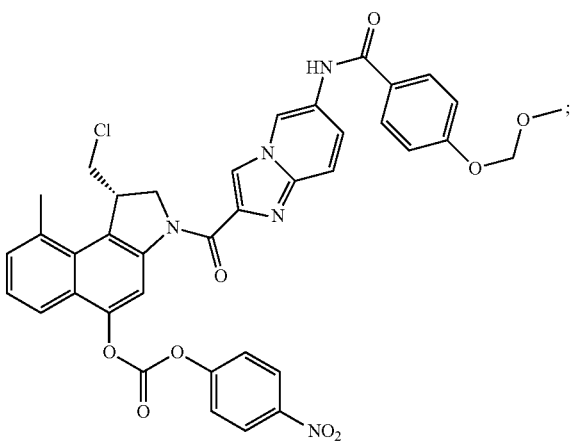 [SMILES: COCOc1ccc(C(=O)Nc2ccc3nc(C(=O)N4C[C@@H](CCl)c5c4cc(OC(=O)Oc4ccc([N+](=O)[O-])cc4)c4cccc(C)c54)cn3c2)cc1]

and the compound of formula (X) is

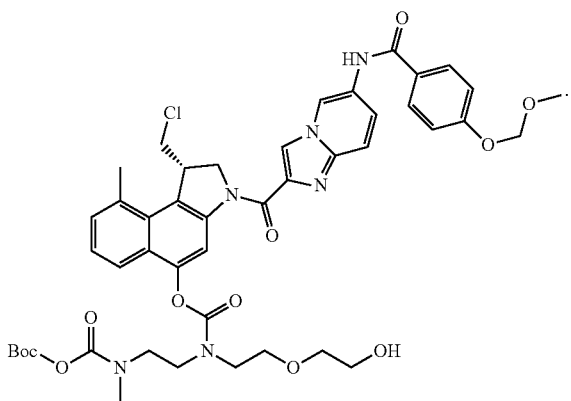 [SMILES: COCOc1ccc(C(=O)Nc2ccc3nc(C(=O)N4C[C@@H](CCl)c5c4cc(OC(=O)N(CCOCCO)CCN(C)C(=O)OC(=O)OC(C)(C)C)c4cccc(C)c54)cn3c2)cc1]

In another embodiment, the process for the synthesis of a linker drug of formula (VIII) further comprises the step of a) deprotecting a compound of formula (X) to obtain a compound of formula (Xa); and b) reacting the compound of formula (Xa) with a compound of formula (XI) in the presence of a base;

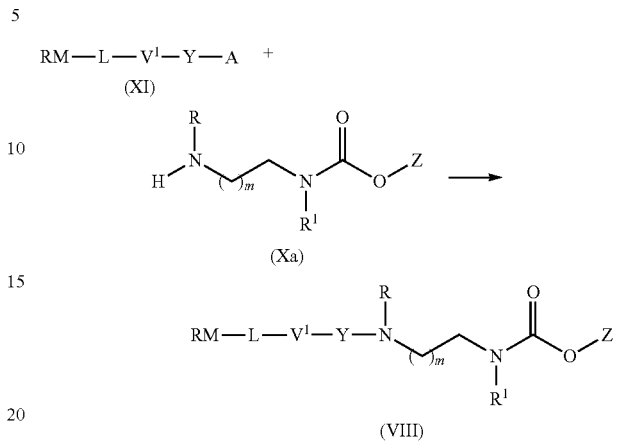

wherein RM, L, V', Y, A, R, $R^1$, Z and m are as defined hereinabove.

The deprotection reaction is performed by treating a compound of formula (X) with an acid in a suitable solvent. A suitable acid for the deprotection reaction is a strong acid. Preferred strong acids are trifluoroacetic acid and hydrochloric acid.

A suitable solvent for the deprotection reaction is a water-free non-protic solvent. Preferably, the solvent is DCM, trichloromethane, 1,2-dichloroethane, toluene, THF, DME, EtOAc or dioxane. The most preferred solvent is DCM.

The reaction between a compound of formula (Xa) with a compound of formula (XI) is performed in the presence of a base in a suitable solvent. A suitable base for the reaction of a compound of formula (Xa) with a compound of formula (XI) is a tertiary amine. A preferred base is triethylamine, diisopropylethylamine, N-methylmorpholine, pyridine or collidine. Most preferred is triethylamine.

A suitable solvent for reacting a compound of formula (Xa) with a compound of formula (XI) is a water-free non-protic solvent, preferably DCM, trichloromethane, 1,2-dichloroethane, toluene, THF, DME, dioxane, EtOAc, acetonitrile, acetone, DMF or DMA. Most preferred is DMF.

Preferably, the process in accordance with the invention is used for the synthesis of a linker drug of formula (VIII) which is

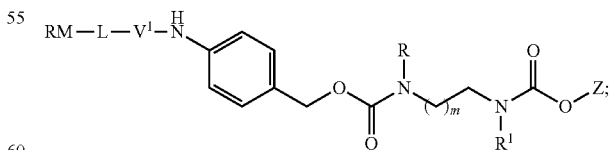

wherein RM, L, $V^1$, R, $R^1$, Z, and m are as defined previously.

More preferably the process in accordance with the invention is used for the synthesis of a linker drug of formula (VIII) which is

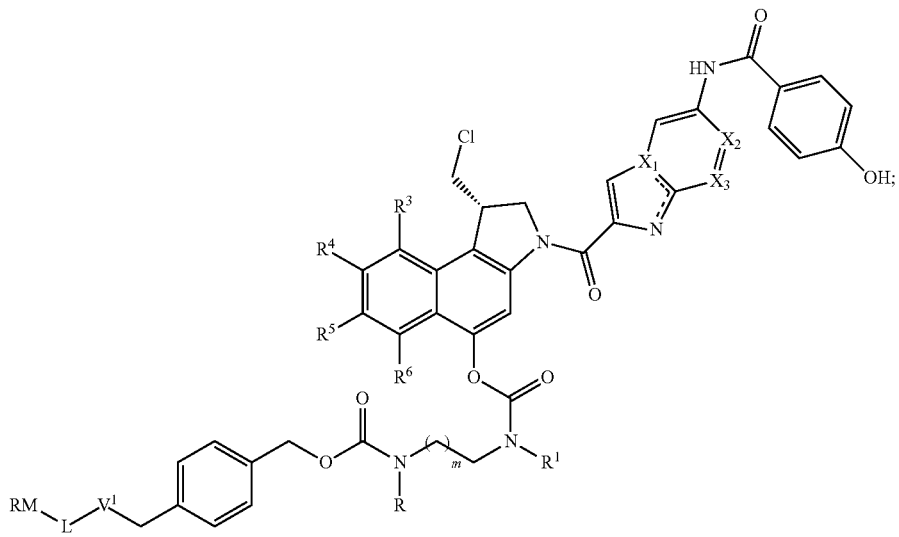

wherein RM, L, $V^1$, R, $R^1$, $R^3$, $R^4$, $R^5$, $R^6$, $X_1$, $X_2$, $X_3$ and m are as defined previously.

More preferably the process in accordance with the invention is used for the synthesis of a linker drug of formula (VIII) which is

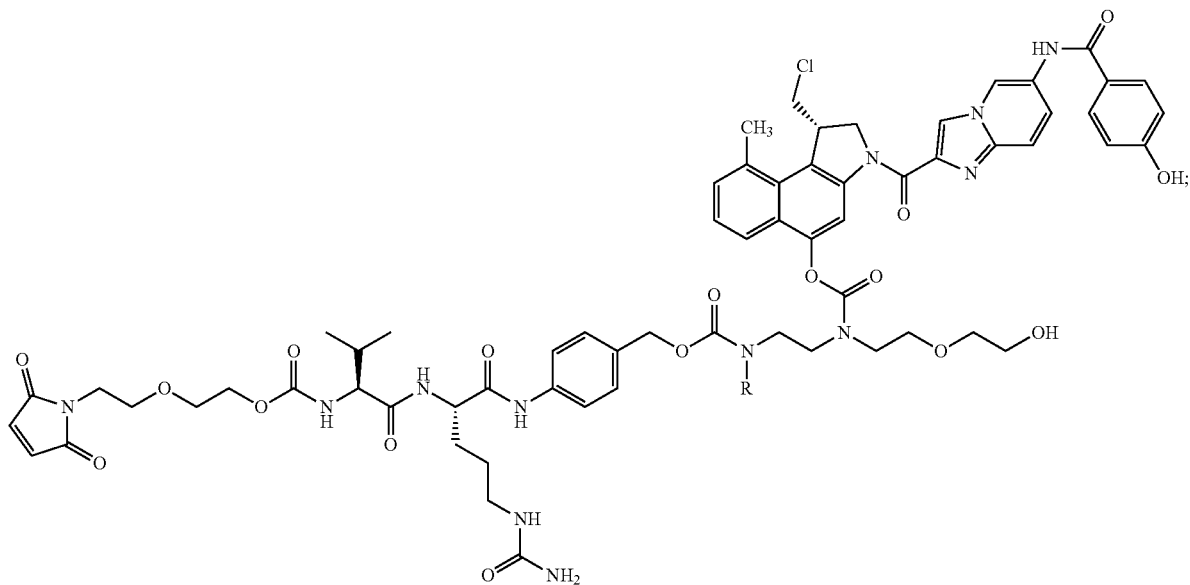

The present invention further relates to the use of the process for the synthesis of a linker drug of formula (VIII) as defined hereinabove in a process for preparing an ADC. The process for preparing an ADC from the linker drug of formula (VIII) can be executed employing procedures and equipment well-known to a person skilled in the art as shown e.g. in Example 15 on page 218 of WO2011133039 and on page 32 of WO2015177360.

In the context of the present invention, any antibody— particularly any antibody known to have therapeutic activity or any antibody known in the art of ADCs, or any antigen-binding fragment thereof, e.g. a F(ab')2 or a Fab' fragment, a single chain (sc) antibody, a scFv, a single domain (sd) antibody, a diabody, or a minibody, can be used for (wild-type or site-specific) conjugation of a linker drug of formula (VIII) as defined hereinabove. Antibodies may be of any isotype such as IgG, IgA or IgM antibodies. Preferably, the antibody is an IgG antibody, more preferably an $IgG_1$ or $IgG_2$ antibody.

The antibody may be a monospecific (i.e. specific for one antigen; such antigen may be common between species or have related antigens between species) antibody or a bispecific (i.e. specific for two different antigens) antibody. In one embodiment of the present invention, the antibody is a monospecific antibody or an antigen-binding fragment thereof.

These antibodies may be produced recombinantly, synthetically, or by other suitable methods known in the art.

Preferably, the antibody binds to an antigen target that is expressed in or on the cell membrane (e.g., on the cell surface) of a tumour cell. More preferably, the antibody is internalised by the cell after binding to the (antigen) target, after which the toxin is released intracellularly.

Typically, an antibody which could be used in the synthesis of an ADC using the process of the present invention includes, but is not limited to an anti-annexin A1 antibody, an anti-B7H4 antibody, an anti-CA6 antibody, an anti-CA9 antibody, an anti-CA15-3 antibody, an anti-CA19-9 antibody, an anti-CA125 antibody, an anti-CA242 antibody, an anti-CCR2 antibody, an anti-CCR5 antibody, an anti-CD2 antibody, an anti-CD19 antibody, an anti-CD20 antibody, an anti-CD22 antibody, an anti-CD30 antibody, an anti-CD33 antibody, an anti-CD37 antibody, an anti-CD38 antibody, an anti-CD40 antibody, an anti-CD44 antibody, an anti-CD47 antibody, an anti-CD56 antibody, an anti-CD70 antibody, an anti-CD74 antibody, an anti-CD79 antibody, an anti-CD115 antibody, an anti-CD123 antibody, an anti-CD138 antibody, an anti-CD203c antibody, an anti-CD303 antibody, an anti-CD333 antibody, an anti-CEA antibody, an anti-CEACAM antibody, an anti-CLCA-1 antibody, an anti-CLL-1 antibody, an anti-c-MET antibody, an anti-Cripto antibody, an anti-CTLA4 antibody, an anti-DLL3 antibody, an anti-EGFL antibody, an anti-EGFR antibody, an anti-EPCAM antibody, anti EPh antibodies, such as an anti-EphA2 antibody or an anti-EPhB3 antibody, an anti-ETBR antibody, an anti-FAP antibody, an anti-FcRL5 antibody, an anti-FGF antibody, an anti-FGFR3, an anti-FOLR1 antibody, an anti-GCC antibody, an anti-GPNMB antibody, an anti-HER2 antibody, an anti-HMW-MAA antibody, an anti-integrin, an anti-IGF1R antibody, an anti-L6 antibody, an anti-Lewis A like carbohydrate antibody, an anti-Lewis X antibody, an anti-Lewis Y antibody, an anti-LIV1 antibody, an anti-mesothelin antibody, an anti-MUC1 antibody, an anti-MUC16 antibody, an anti-NaPi2b antibody, an anti-Nectin-4 antibody, an anti-PSMA antibody, an anti-PTK7 antibody, an anti-SLC44A4 antibody, an anti-STEAP-1 antibody, an anti-5T4 (or anti-TPBG, trophoblast glycoprotein) antibody, an anti-TF (tissue factor) antibody, an anti-TF-Ag antibody, an anti-Tag72 antibody, an anti-TNF antibody, an anti-TROP2 antibody, an anti-VEGF antibody, and an anti-VLA antibody.

In a preferred embodiment of the invention, the antibody is an anti-HER2 antibody, preferably trastuzumab.

In a further preferred embodiment of the invention, the antibody-drug conjugate is

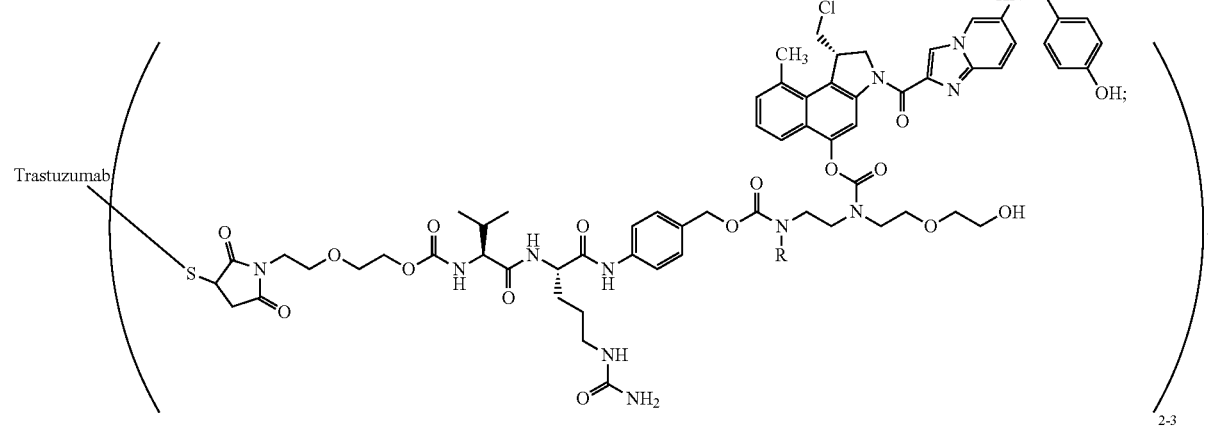

In an alternative embodiment, the invention relates to a process for the synthesis of a compound of formula (III)

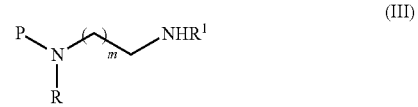

comprising the steps of
a) converting a compound of formula (V) into a compound of formula (VI) by reacting a compound of formula (V) with a compound of formula (VII) in the presence of a coupling reagent

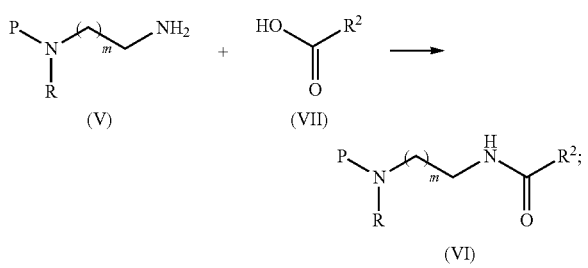

b) treating, the compound of formula (VI) with a borane reagent, followed by acid hydrolysis;
wherein R is selected from H, $(CH_2)_nOCH_3$, $(CH_2CH_2O)_nH$, $(CH_2CH_2O)_nCH_3$, $(CH_2)_nNHP$, $(CH_2)_nN(CH_3)_2$, $(CH_2)_nNHCONH_2$, $(CH_2)_nNHSO_2CH_3$, $(CH_2)_nSO_2NH_2$, optionally substituted $C_{1-8}$ alkyl, optionally substituted $C_{3-15}$ cycloalkyl and optionally substituted $C_{3-15}$ heterocycloalkyl;

$R^2$ is selected from H, $(CH_2)_{n-1}OCH_3$, $CH_2O(CH_2CH_2O)_{n-1}H$, $CH_2O(CH_2CH_2O)_{n-1}CH_3$, $(CH_2)_{n-1}NHP$, $(CH_2)_{n-1}N(CH_3)_2$, $(CH_2)_{n-1}NHCONH_2$, $(CH_2)_{n-1}NHSO_2CH_3$, $(CH_2)_{n-1}SO_2NH_2$, and optionally substituted $C_{1-7}$ alkyl;

P is a protective group as defined hereinabove;

m is an integer of from 1 to 3; and n is an integer of from 1 to 12.

The starting materials of the above process, i.e. compounds of formula (V) and (VII) are either commercially available or can be produced by methods and procedures well-known in the prior art.

The transformation of compound (VI) into compound (III) involves the reduction of the carbonyl group external to the diamino alkyl chain generating a $CH_2R^2$ substituent,

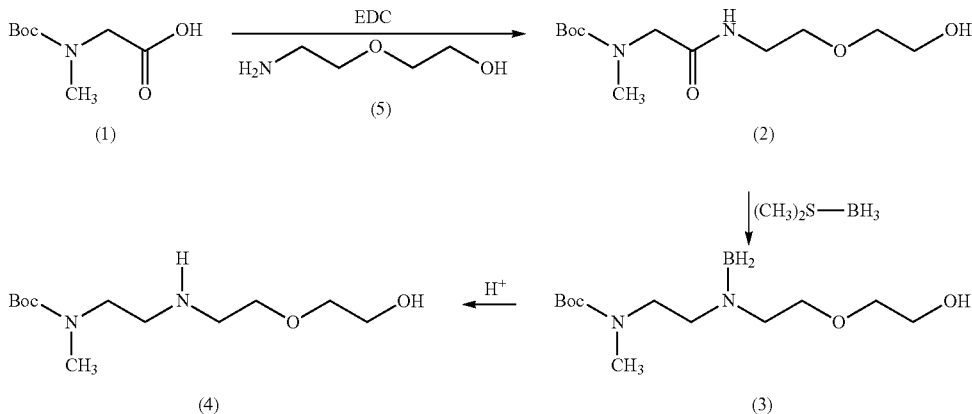
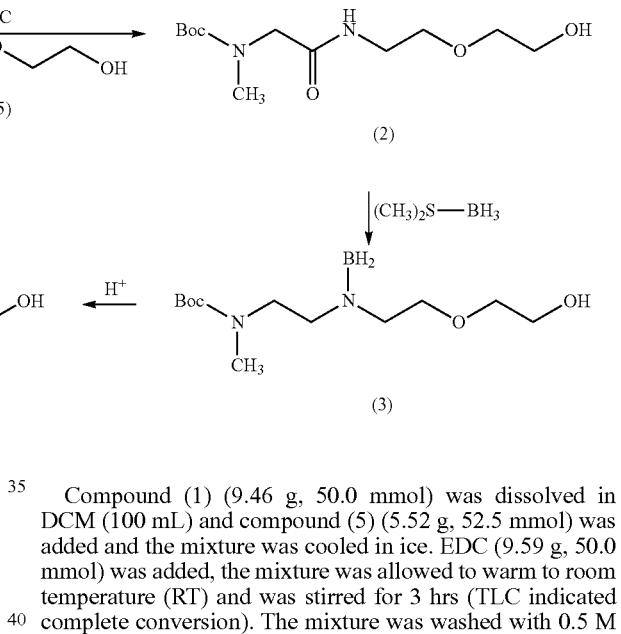

which corresponds to the $R^1$ substituent of a compound of formula (III). The design of the alternative process also allows the combination of a high yielding peptide coupling step and an efficient boron reduction step.

In a preferred embodiment of the present invention, R is $C_{1-8}$ alkyl and $R^2$ is selected from H, $(CH_2)_{n-1}OCH_3$, $CH_2O(CH_2CH_2O)_{n-1}H$, $CH_2O(CH_2CH_2O)_{n-1}CH_3$, $(CH_2)_{n-1}NHP$, $(CH_2)_{n-1}N(CH_3)_2$, $(CH_2)_{n-1}NHCONH_2$, $(CH_2)_{n-1}NHSO_2CH_3$, $(CH_2)_{n-1}SO_2NH_2$, and optionally substituted $C_{1-7}$ alkyl; wherein n is an integer of from 1 to 12, preferably n is an integer of from 1 to 6.

In a second preferred embodiment of the present invention, R is $CH_3$ and $R^2$ is selected from $(CH_2)_{n-1}OCH_3$, $CH_2O(CH_2CH_2O)_{n-1}H$, $CH_2O(CH_2CH_2O)_{n-1}CH_3$, and optionally substituted $C_{1-7}$ alkyl; wherein n is an integer of from 1 to 12, preferably n is an integer of from 1 to 6.

In a third preferred embodiment of the present invention, R is $CH_3$ and $R^2$ is selected from $CH_2O(CH_2CH_2O)_{n-1}H$, $CH_2O(CH_2CH_2O)_{n-1}CH_3$, and optionally substituted $C_{1-7}$ alkyl; wherein n is an integer of from 1 to 12, preferably n is an integer of from 1 to 6.

The process conditions for the coupling reaction, the reaction with the borane reagent and the acid hydrolysis are similar as described hereinabove for the process starting from a compound of formula (I).

Additionally, the alternative process starting from a compound of formula (V) can be used in the process for the synthesis of a compound of formula (VIII) as described hereinabove and in a process for the synthesis of an ADC.

EXAMPLES

Example 1

Preparation of compound (4), a compound of formula (III), from compounds (1), a compound of formula (I), and (5), a compound of formula (IV) according to the following Scheme:

Compound (1) (9.46 g, 50.0 mmol) was dissolved in DCM (100 mL) and compound (5) (5.52 g, 52.5 mmol) was added and the mixture was cooled in ice. EDC (9.59 g, 50.0 mmol) was added, the mixture was allowed to warm to room temperature (RT) and was stirred for 3 hrs (TLC indicated complete conversion). The mixture was washed with 0.5 M $KHSO_4$ solution (25 mL), dried with $MgSO_4$ and concentrated in vacuo to give 11.81 g compound (2) as a colorless oil (85% yield) (chemically pure by TLC and NMR).

$^1$H-NMR (300 MHz, $CDCl_3$): δ=1.47 (s, 9H, Boc), 2.75 (br s, 1H, OH), 2.94 (s, 3H, MeN), 3.48 (br q, 2H, $NCH_2$), 3.58 (m, 4H, $OCH_2$), 3.73 (m, 2H, $OCH_2$), 3.86 (s, 2H, $NCH_2C=O$), 6.68 (br d, 1H, NH).

Compound (2) (11.39 g, 41.2 mmol) was dissolved in dry THF (200 mL) and cooled in ice. Next, borane dimethyl-sulfide (19 mL, 200 mmol) was added dropwise and stirred at RT overnight. The reaction mixture was carefully quenched with MeOH (50 mL) followed by water addition (50 mL). The THF/MeOH was evaporated and the residue basified with NaOH (4M, 50 mL) and extracted with DCM (4×50 mL). Then, the combined organic layers were dried using a drying agent (e.g. $MgSO_4$), filtered and concentrated in vacuo to give 11.76 g of the borane-intermediate (3) (99%). The borane-intermediate (3) (11.76 g, 41.2 mmol) was dissolved in MeOH (100 mL), 4-toluenesulfonic acid hydrate (8.98 g, 47.2 mmol) was added and the mixture was stirred for 4 hrs at RT. The mixture was basified with NaOH (4M, 12 mL) and concentrated in vacuo. The residue was extracted with DCM (4×50 mL) and then, the combined organic layers were washed with NaOH (4M, 50 mL), dried using a drying agent (e.g. $MgSO_4$), filtered and concentrated in vacuo to give 8.95 g of compound (4) (80% yield, chemical purity 94%) as a colorless oil.

$^1$H NMR (300 MHz, CDCl$_3$): δ=1.46 (s, 9H, Boc), 2.18 (br s, 2H, OH+NH), 2.75-2.87 (m, 4H, 2×CH$_2$), 2.88 (s, 3H, NMe), 3.35 (t, 2H, J=6.6 Hz, CH$_2$), 3.56-3.63 (m, 4H, 2×CH$_2$, CH), 3.70-3.75 (m, 2H, CH$_2$, CH); MS (ESI) m/z=263.5 (M+H$^+$).

Example 2

Compounds of formula (III) obtained by the procedures of example 2 were converted to linker-drug compounds of formula (XII) according to the procedure of Example 10 on page 209 of WO2011133039.

The invention claimed is:
1. A process comprising the steps of
   a) Converting a compound of formula (I) into a compound of formula (II) by reacting a compound of formula (I) with a compound of formula (IV) in the presence of a coupling reagent and
   b) Treating the compound of formula (II) with a borane reagent, followed by acid hydrolysis to form a compound of formula (III)

wherein R and R$^1$ are independently selected from H, (CH$_2$)$_n$OCH$_3$, (CH$_2$CH$_2$O)$_n$H, (CH$_2$CH$_2$O)$_n$CH$_3$, (CH$_2$)$_n$NHP, (CH$_2$)$_n$N(CH$_3$)$_2$, (CH$_2$)$_n$NHCONH$_2$, (CH$_2$)$_n$NHSO$_2$CH$_3$, (CH$_2$)$_n$SO$_2$NH$_2$, optionally substituted C$_{1-8}$ alkyl, optionally substituted C$_{3-15}$ cycloalkyl and optionally substituted C$_{3-15}$ heterocycloalkyl;
   P is a protective group;
   m is an integer of from 1 to 3; and
   n is an integer of from 1 to 12.
2. The process according to claim 1, wherein R is C$_{1-8}$ alkyl and R$^1$ is selected from H, (CH$_2$)$_n$OCH$_3$, (CH$_2$CH$_2$O)$_n$H, (CH$_2$CH$_2$O)$_n$CH$_3$, (CH$_2$)$_n$NHP, (CH$_2$)$_n$N(CH$_3$)$_2$, (CH$_2$)$_n$NHCONH$_2$, (CH$_2$)$_n$NHSO$_2$CH$_3$, (CH$_2$)$_n$SO$_2$NH$_2$, optionally substituted C$_{1-8}$ alkyl, optionally substituted C$_{3-15}$ cycloalkyl and optionally substituted C$_{3-15}$ heterocycloalkyl.
3. The process according to claim 1, wherein R is CH$_3$ and R$^1$ is selected from (CH$_2$)$_n$OCH$_3$, (CH$_2$CH$_2$O)$_1$H, (CH$_2$CH$_2$O)CH$_3$ and optionally substituted C$_{1-8}$ alkyl.
4. The process according to claim 1, wherein the coupling reagent is selected from the group consisting of carbodiimide reagents, phosphonium reagents and aminium reagents.
5. The process according to claim 1, wherein the borane reagent is borane, diborane or a borane-ligand complex.
6. The process according to claim 5, wherein the borane reagent is a borane-ligand complex selected from borane tetrahydrofuran or borane dimethyl sulfide.
7. The process according to claim 1, wherein the protective group P is selected from the group consisting of 1,1-dimethyl-2-haloethyl carbamate, 1,1-dimethyl-2,2-dibromoethyl carbamate, t-butyl carbamate, 1-adamantyl carbamate, N-(2-pivaloylamino)-1,1-dimethylethyl carbamate, 2-[(2-nitrophenyl)dithio]-1-phenylethyl carbamate, 9-anthrylmethyl carbamate, methyl carbamate, ethyl carbamate, p-methoxybenzyl carbamate, N-hydroxypiperidinyl, p-nitrobenzyl carbamate, diphenylmethyl carbamate, m-chloro-p-acyloxybenzyl carbamate, p-(dihydroxyboryl) benzyl carbamate, 5-benzisoxazolylmethyl carbamate, benzyl, N-2,4,6-trimethylbenzenesulfonyl, N-toluenesulfonyl, N-benzylsulfonyl and N-trifluoromethylsulfonyl.
8. The process according to claim 7, wherein the protective group P is selected from the group consisting of 1,1-dimethyl-2-haloethyl carbamate, 1,1-dimethyl-2,2-dibromoethyl carbamate, t-butyl carbamate, 1-adamantyl carbamate, N-(2-pivaloylamino)-1,1-dimethylethyl carbamate, 2-[(2-nitrophenyl)dithio]-1-phenylethyl carbamate and 9-anthrylmethyl carbamate.
9. The process according to claim 1, wherein the acid hydrolysis is performed with an acid selected from the group consisting of alkyl or optionally substituted alkyl sulfonic acid, aryl or optionally substituted aryl sulfonic acid, potassium hydrogen sulphate, sulphuric acid, hydrochloric acid, hydrobromic acid, phosphoric acid, trifluoroacetic acid, trichloroacetic acid, chloroacetic acid, phosphonic acid, benzyl phosphonic acid, acetic acid and formic acid.
10. The process according to claim 9, wherein the acid hydrolysis is performed with an acid selected from the group consisting of alkyl or optionally substituted alkyl sulfonic acid and aryl or optionally substituted aryl sulfonic acid.
11. The process according to claim 1, wherein the compound of formula (III) is 12. The process according to claim 1, which further comprises the step of reacting a compound of formula (IX) with the compound of formula (III) to provide a compound of formula (X)

wherein A is an activated carbonate moiety;
Z' is Z or Z' is Z comprising one or more alcohol-protective groups P' when Z comprises more than one alcohol function; and
Z is a therapeutic or diagnostic moiety.

13. The process according to claim 12, which further comprises the steps of
   a) Deprotecting the compound of formula (X) to obtain a compound of formula (Xa); and
   b) Reacting the compound of formula (Xa) with a compound of formula (XI) in the presence of a base to form a linker drug of formula (VIII)

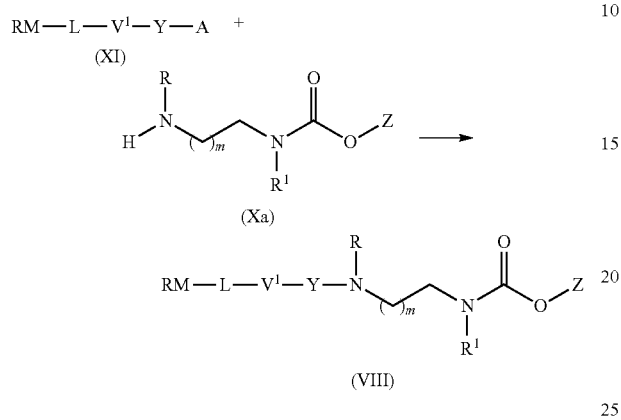

wherein RM is a reactive moiety;
L is a linking group linking RM to $V^1$;
$V^1$ is a peptide, a mono, di-, or oligosaccharide; and
Y is either absent or an electronic cascade spacer.

14. The process according to claim 13, which further comprises reacting the linker drug of formula (VIII) with an antibody or an antigen-binding fragment thereof to form an antibody drug conjugate.

15. The process according to claim 4, wherein the coupling reagent is a carbodiimide reagent.

16. The process according to claim 15, wherein the borane reagent is borane, diborane or a borane-ligand complex.

17. The process according to claim 16, wherein the borane reagent is a borane-ligand complex selected from borane tetrahydrofuran or borane dimethyl sulfide.

18. The process according to claim 17, wherein the protective group P is selected from the group consisting of 1,1-dimethyl-2-haloethyl carbamate, 1,1-dimethyl-2,2-dibromoethyl carbamate, t-butyl carbamate, 1-adamantyl carbamate, N-(2-pivaloylamino)-1,1-dimethylethyl carbamate, 2-[(2-nitrophenyl)dithio]-1-phenylethyl carbamate and 9-anthrylmethyl carbamate.

19. The process according to claim 18, wherein the compound of formula (III) is

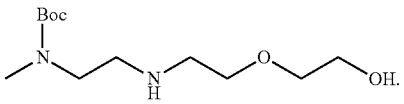 [SMILES: CN(CCNCCOCCO)C(=O)OC(C)(C)C]

20. The process according to claim 18, wherein said coupling reagent is EDC (1-[(3-dimethylaminopropyl)]-3-ethylcarbodiimide hydrochloride).

* * * * *